United States Patent
Kang et al.

(10) Patent No.: US 11,249,549 B2
(45) Date of Patent: Feb. 15, 2022

(54) BRAIN CONNECTIVITY-BASED VISUAL PERCEPTION TRAINING DEVICE, METHOD AND PROGRAM

(71) Applicant: NUNAPS INC., Seoul (KR)

(72) Inventors: Dong Wha Kang, Seoul (KR); Dong Ho Kim, Seoul (KR)

(73) Assignee: NUNAPS INC., Seoul (KR)

( * ) Notice: Subject to any disclaimer, the term of this patent is extended or adjusted under 35 U.S.C. 154(b) by 0 days.

(21) Appl. No.: 16/931,017

(22) Filed: Jul. 16, 2020

(65) Prior Publication Data

US 2020/0348756 A1 Nov. 5, 2020

Related U.S. Application Data

(63) Continuation of application No. PCT/KR2019/000772, filed on Jan. 18, 2019.

(30) Foreign Application Priority Data

Jan. 18, 2018 (KR) .......................... 10-2018-0006546

(51) Int. Cl.
*G06F 3/01* (2006.01)
*G02B 27/00* (2006.01)
(Continued)

(52) U.S. Cl.
CPC ......... *G06F 3/015* (2013.01); *G02B 27/0093* (2013.01); *G02B 27/0172* (2013.01);
(Continued)

(58) Field of Classification Search
None
See application file for complete search history.

(56) References Cited

U.S. PATENT DOCUMENTS 10,258,259 B1 * 4/2019 Zets .................. A61H 5/00
2008/0278682 A1 * 11/2008 Huxlin ................ A61H 5/00
351/203
(Continued)

FOREIGN PATENT DOCUMENTS

JP          2008-534157 A    8/2008
KR          10-0283526 B     3/2001
(Continued)

OTHER PUBLICATIONS

International Search Report issued in PCT/KR2019/000772; dated Apr. 16, 2019.

*Primary Examiner* — Jwalant Amin
(74) *Attorney, Agent, or Firm* — Studebaker & Brackett PC (57) ABSTRACT

The present invention relates to a brain connectivity-based visual perception training device, method and program. The brain connectivity-based visual perception training method, according to one embodiment of the present invention, comprises: a step (S200; a spatial movement image providing step) of allowing a computer to provide a spatial movement image to a head-mounted display device; a step (S400; a visual perception training image providing step) of allowing the computer to provide a visual perception training image simultaneously with the spatial movement image or subsequently to the spatial movement image; and a step (S1000) of allowing the computer to receive, from a user, a performance result of a first task of the visual perception training image. Hereinafter, each step is described in detail.

20 Claims, 5 Drawing Sheets

(51) Int. Cl.
*G02B 27/01* (2006.01)
*G06T 19/00* (2011.01)

(52) U.S. Cl.
CPC ......... *G02B 27/0179* (2013.01); *G06F 3/013* (2013.01); *G06T 19/006* (2013.01); *G02B 2027/0187* (2013.01); *G06F 2203/012* (2013.01)

(56) References Cited

U.S. PATENT DOCUMENTS

| | | | | |
|---|---|---|---|---|
| 2009/0062092 | A1* | 3/2009 | Mortimer | A63B 26/003 482/142 |
| 2012/0218285 | A1* | 8/2012 | Crane | A61B 5/4023 345/589 |
| 2012/0257797 | A1* | 10/2012 | Leyvand | A63F 13/40 382/118 |
| 2014/0270182 | A1* | 9/2014 | Vilermo | H04S 7/303 381/17 |
| 2015/0058812 | A1* | 2/2015 | Lindh | G02B 27/00 715/863 |
| 2016/0063762 | A1* | 3/2016 | Heuvel | G06K 9/52 345/633 |
| 2016/0192009 | A1* | 6/2016 | Sugio | G06K 9/3241 725/32 |
| 2016/0299563 | A1* | 10/2016 | Stafford | G06F 3/011 |
| 2018/0061127 | A1* | 3/2018 | Gullicksen | G06F 3/0383 |
| 2019/0217046 | A1* | 7/2019 | Kang | A61B 5/162 |
| 2019/0232113 | A1* | 8/2019 | Zets | A63B 24/0075 |

FOREIGN PATENT DOCUMENTS

| | | |
|---|---|---|
| KR | 10-1381134 B1 | 4/2014 |
| KR | 10-2015-0118242 A | 10/2015 |
| KR | 10-1764061 B1 | 8/2017 |

* cited by examiner

FIG. 1

(S200) Step of allowing computer to provide spatial movement image to head-mounted display device (S400) Step of allowing computer to provide visual perception training image simultaneously with spatial movement image or subsequently to spatial movement image (S1000) Step of allowing computer to receive, from user, performance result of first task of visual perception training image

(S200) Step of allowing computer to provide spatial movement image to head-mounted display device (S400) Step of allowing computer to provide visual perception training image simultaneously with spatial movement image or subsequently to spatial movement image (S700) Step of allowing computer to output sound in direction corresponding to location where task image is displayed (S1000) Step of allowing computer to receive, from user, performance result of first task of visual perception training image

FIG. 7

(S200) Step of allowing computer to provide spatial movement image to head-mounted display device

(S400) Step of allowing computer to provide visual perception training image simultaneously with spatial movement image or subsequently to spatial movement image (S800) Step of allowing computer to obtain gaze direction of user (S900) Step of allowing computer to determine display location in task image of visual perception training image on training area within field of view on the basis of gaze direction (S1000) Step of allowing computer to receive, from user, performance result of first task of visual perception training image

FIG. 8

BRAIN CONNECTIVITY-BASED VISUAL PERCEPTION TRAINING DEVICE, METHOD AND PROGRAM

CROSS-REFERENCE TO RELATED APPLICATIONS

The present application is a continuation of International Patent Application No. PCT/KR2019/000772, filed Jan. 18, 2019, which is based upon and claims the benefit of priority to Korean Patent Application No. 10-2018-0006546, filed on Jan. 18, 2018. The disclosures of the above-listed applications are hereby incorporated by reference herein in their entirety.

BACKGROUND

Embodiments of the inventive concept described herein relate to a brain connectivity-based visual perception training device, method, and program, and more particularly, relate to a device for improving a visual perception function degraded by degradation or damage to a brain function, a method therefor, and a program therefor.

In general, the stroke is No. 1 domestic cause of the disabled as a single disease. A visual field defect among brain function damages due to the stroke is a major disorder indicating a high rate of 20% to 30% of all patients. Because such a visual field defect is usually accepted as a permanent loss, the reality is that there is no attempt itself to rehabilitate the visual field defect. A patient who has a brain injury in the visual cortex according to the stroke typically shows hemianopia at an opposite side of the lesion. For example, a patient who has the stroke in a left visual cortex portion shows hemianopia at the right side. At this time, when the patient looks at the front with his or her eyes open, he or she does not recognize a thing or motion present in the right field of view.

However, there is a patient who perceives any motion or form in his or her field of view which is not seen among patients with the visual field defect due to the stroke which occurs in the visual cortex portion. In this case, when letting the patient to see X or O in the field of view which is not seen and answer a character, the patient answers, "I can't see.", probabilistically answers the character over a chance level, and even shows a response suitable for a visual stimulus. Such a patient does not perceive stimuli visually, but his or her brain perceives the motion or form. This phenomenon discovered by Lawrence Weiskrantz of the 1970s is called blindsight. The blindsight refers to a phenomenon where a person perceives a thing although not seen.

The presence of the blindsight phenomenon suggests that visual information input via retinas may be processed through another place rather than the visual cortex.

Thus, there is a need for a visual perception training method and apparatus for performing visual perception learning (training) by repeatedly providing a visual perception stimulus to improve a visual perception function.

SUMMARY

Embodiments of the inventive concept provide a brain connectivity-based visual perception training device for enhancing an effect of improving a visual perception function by training the hippocampus having connectivity with the visual cortex together with providing a visual perception training image, a method therefor, and a program therefor.

The technical problems to be solved by the inventive concept are not limited to the aforementioned problems, and any other technical problems not mentioned herein will be clearly understood from the following description by those skilled in the art to which the inventive concept pertains.

According to an exemplary embodiment, a brain connectivity-based visual perception training method may include providing, by a computer, a spatial movement image to a head-mounted display device, the spatial movement image being an image where a user moves along a path in a virtual space, providing, by the computer, a visual perception training image simultaneously with the spatial movement image or subsequently to the spatial movement image, and receiving, by the computer, the result of performing a first task of the visual perception training image from the user.

Furthermore, as another embodiment, the providing of the visual perception training image may include, when providing the visual perception training image subsequently to the spatial movement image, generating and providing, by the computer, the visual perception training image based on a condition assigned to each space, when the user enters any one of a plurality of spaces present in the virtual space by moving along the path.

Furthermore, as another embodiment, the brain connectivity-based visual perception training method may further include requesting, by the computer, the user to perform a second task entering the same space as that in previous performance and calculating, by the computer, a final result by reflecting the result of performing the second task in the result of performing the first task, when the user succeeds in performing the second task.

Furthermore, as another embodiment, the providing of the visual perception training image may include, when providing the visual perception training image simultaneously with the spatial movement image, combining and providing frames of the visual perception training image, the frames being generated at intervals of a unit time, on the spatial movement image.

Furthermore, as another embodiment, the first task may be a task which should be performed by the user upon walking and may be displayed on a visual perception training area of the user in the visual perception training image. The result of performing the first task may be whether the user who is walking performs motion corresponding to the first task.

Furthermore, as another embodiment, the providing of the visual perception training image may include generating a final output image by combining a first image frame included in the spatial movement image with a second image frame included in the visual perception training image. The first image frame may be changed by head motion or pupil motion of the user. The second image frame may be fixed without being changed by the head motion or the pupil motion of the user.

Furthermore, as another embodiment, the spatial movement image may be generated based on data obtained by sensing real walking of the user using a walking sensing device.

Furthermore, as another embodiment, the visual perception training image may display a task image on a visual perception training area of the user in the visual perception training image. The brain connectivity-based visual perception training method may further include outputting, by the computer a sound in a direction corresponding to a location where the task image is displayed.

Furthermore, as another embodiment, the brain connectivity-based visual perception training method may further obtaining, by the computer, a gaze direction of the user and determining, by the computer, a display location in a task image of the visual perception training image on a training area in a field of view on the basis of the gaze direction.

According to an exemplary embodiment, a brain connectivity-based visual perception training program may be combined with a computer which is hardware and may be stored in a medium to execute the above-mentioned brain connectivity-based visual perception training method.

According to an exemplary embodiment, a brain connectivity-based visual perception training computing device may include a communication unit that provides a spatial movement image to a client device connected with a head-mounted display device or the head-mounted display device and a controller that provides a visual perception training image simultaneously with the spatial movement image or subsequently to the spatial movement image, receives the result of performing a first task of the visual perception training image from a user, and calculates a final result of visual perception training. The spatial movement image may be an image where the user moves along a path in a virtual space.

Furthermore, as another embodiment, when providing the spatial movement image as the user moves along the path in the virtual space and when providing the visual perception training image subsequently to the spatial movement image as the user enters any one of a plurality of divided spaces present in the virtual space, the controller may generate the virtual perception training image depending on a virtual perception training image providing condition assigned to each divided space the user enters. The virtual perception training image providing condition may be whether the visual perception training image is provided in each divided space or a level of a reward provided when the visual perception training image is performed in each divided space.

Furthermore, as another embodiment, the controller may request the user to perform a second task entering the same space as that in previous performance and may calculate a final result by reflecting the result of performing the second task in the result of performing the first task, when the user succeeds in performing the second task.

Furthermore, as another embodiment, the controller may simultaneously provide the spatial movement image as the user moves along the path and the visual perception training image displaying the first task on a visual perception training area and may receive motion of the user, the motion corresponding to the first task, while the user moves along the path, and may calculate the result of performing the first task.

Furthermore, as another embodiment, the controller may generate the spatial movement image based on data obtained by sensing real walking of the user using a walking sensing device.

According to an exemplary embodiment, a head-mounted display device may include providing a spatial movement image on a screen of the head-mounted display device, providing a visual perception training image, including a first task, simultaneously with the spatial movement image or subsequently to the spatial movement image, and calculating a final result of visual perception training based on the result of performing the first task of the visual perception training image or transmitting the result of performing the first task to a computing device configured to calculate the final result. The result of performing the first task may be generated by determining whether a user operation received from a user is identical to the first task. The user operation may be input via a controller connected with the head-mounted display device. The spatial movement image may be an image where the user moves along a path in a virtual space.

According to an exemplary embodiment, a brain connectivity-based visual perception training device may include providing a spatial movement image providing path movement of a user in a virtual space, providing a visual perception training image simultaneously with the spatial movement image or subsequently to the spatial movement image, and receiving the result of performing a first task of the visual perception training image from the user.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereinafter, an embodiment of the inventive concept will be described in detail with reference to the accompanying drawings. Advantages, features, and methods of accomplishing the same will become apparent with reference to embodiments described in detail below together with the accompanying drawings. However, the inventive concept is not limited by embodiments disclosed hereinafter, and may be implemented in various forms. Rather, these embodiments are provided to so that this disclosure will be through and complete and will fully convey the concept of the invention to those skilled in the art, and the inventive concept will only be defined by the appended claims. The same reference denotations refer to the same components throughout the specification.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

Terms used in the specification are used to describe embodiments of the inventive concept and are not intended to limit the scope of the inventive concept. In the specification, the terms of a singular form may include plural forms unless otherwise specified. The expressions "comprise" and/or "comprising" used herein indicate existence of one or more other elements other than stated elements but do not exclude presence of additional elements.

The computer in the specification may include all of various devices capable of performing arithmetic processing and providing a user with the result of performing the arithmetic processing. For example, the computer may correspond to a smartphone, a tablet personal computer (PC), a cellular phone, a personal communication service (PCS) phone, a synchronous/asynchronous international mobile telecommunication-2000 (IMT-2000) mobile phone, a palm PC, a personal digital assistant (PDA), or the like as well as a desktop PC or a note book. Furthermore, when a head mounted display (HMD) device includes a computing function, it may be the computer. Furthermore, the computer may correspond to a server which receives a request from a client and performs information processing.

The 'visual perception training area' in the specification refers to an area where a visual perception function should be improved by visual perception training within a field of view. For example, for a patient with a visual field defect by brain damage, the 'visual perception training area' may be a specific area which is not seen within a field of view due to brain damage.

The 'spatial movement image' in the specification refers to an image representing movement in a virtual space of a user.

The 'visual perception training image' in the specification refers to an image presenting a task to a visual perception training area to perform visual perception training.

The 'first task' in the specification refers to a task provided in the visual perception training image.

The 'second task' in the specification is a task provided to the user through a spatial movement image, which refers to a task evaluating a spatial memory of the user.

Hereinafter, a description will be given in detail of a brain connectivity-based visual perception training device, method, and program according to embodiments of the inventive concept with reference to the drawings.

Figure 1:
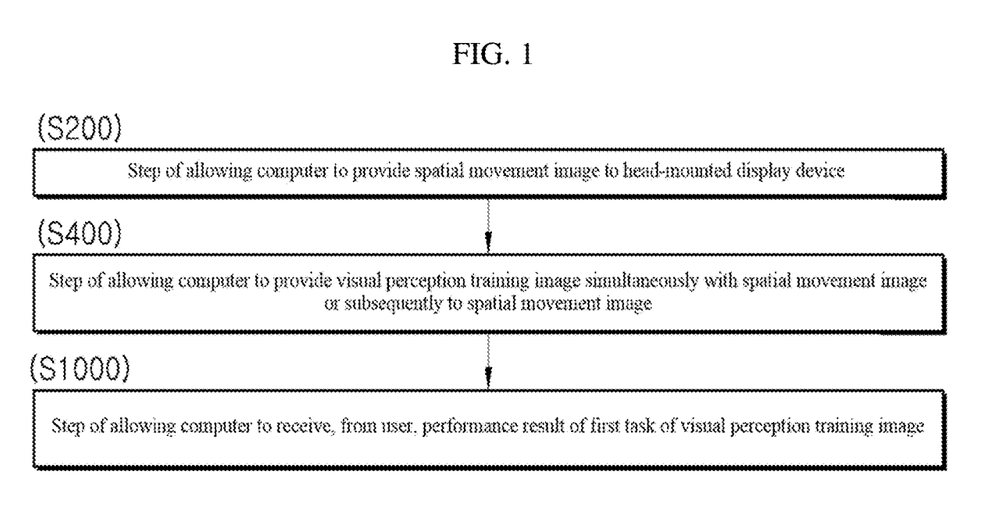
FIG. 1 is a flowchart illustrating a brain connectivity-based visual perception training method according to an embodiment of the inventive concept.
Figure 2:
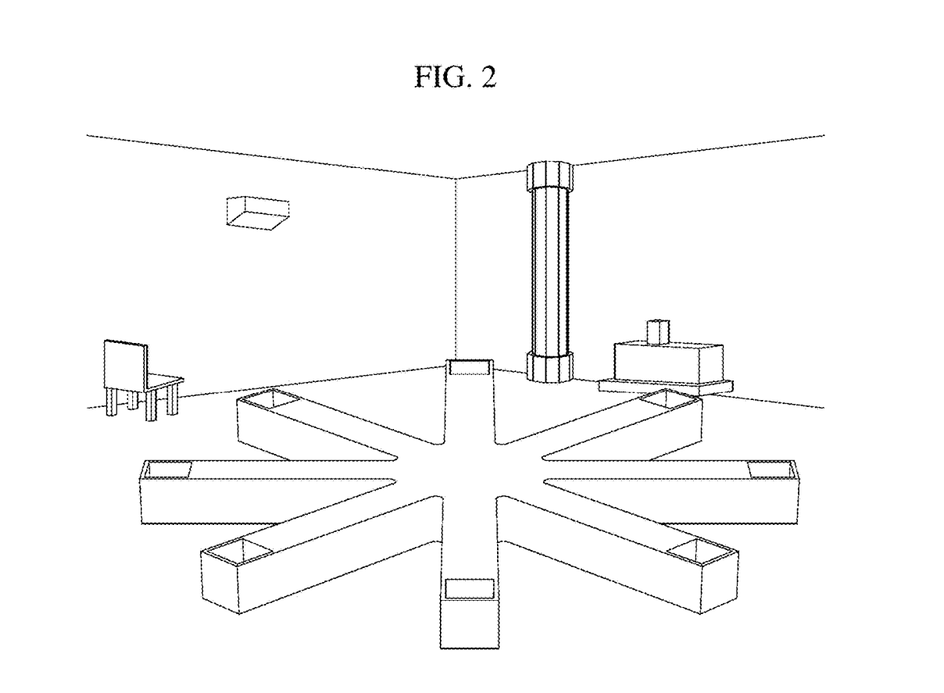
FIG. 2 is a drawing illustrating a radial maze which is a virtual space for generating a spatial movement image according to an embodiment of the inventive concept.
Figure 3A:
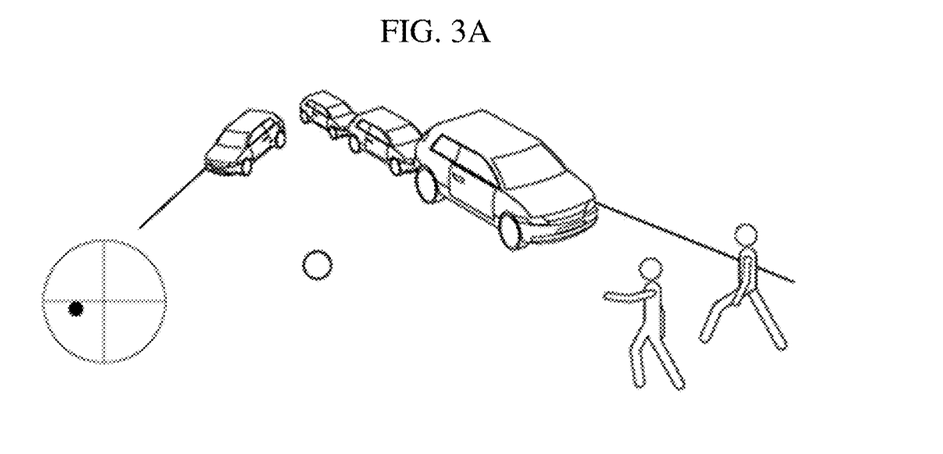
FIG. 3A is a drawing illustrating a field of view seen by a normal person.
Figure 3B:
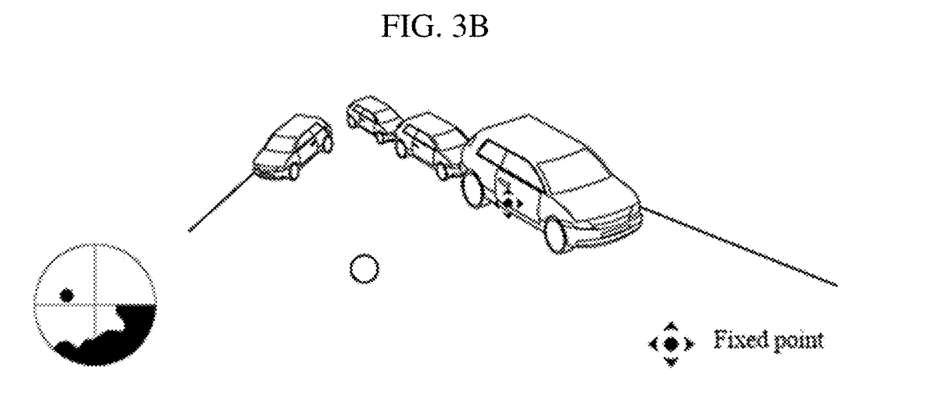
FIGS. 3B and 3C are drawings illustrating a field of view seen by a patient with a visual perception disability according to brain damage.
Figure 3C:
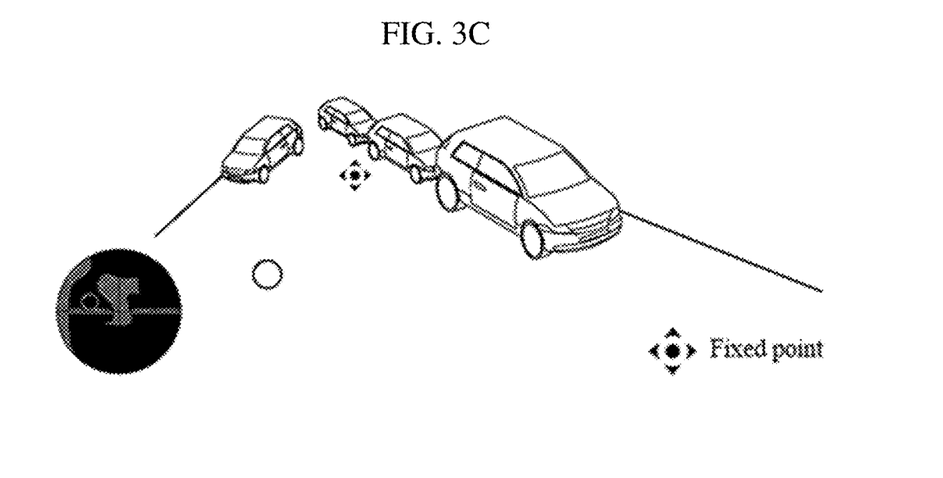
Figure 4:
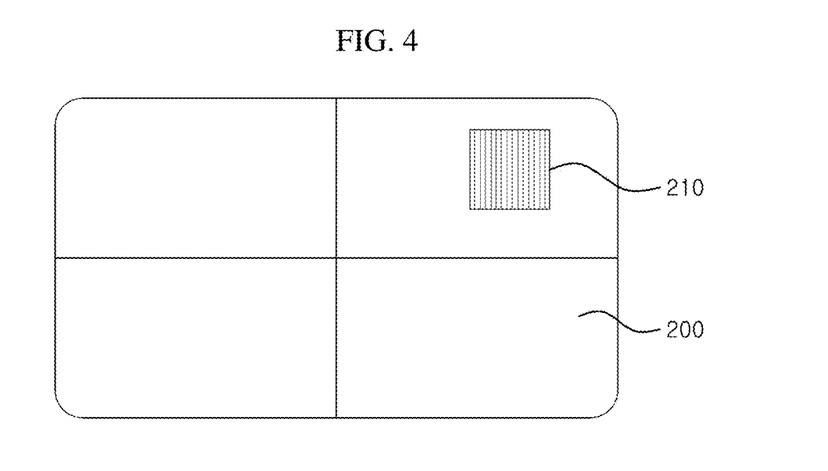
FIG. 4 is a drawing illustrating a visual perception training image provided in a specific space after performing spatial movement according to an embodiment of the inventive concept.
Figure 5:
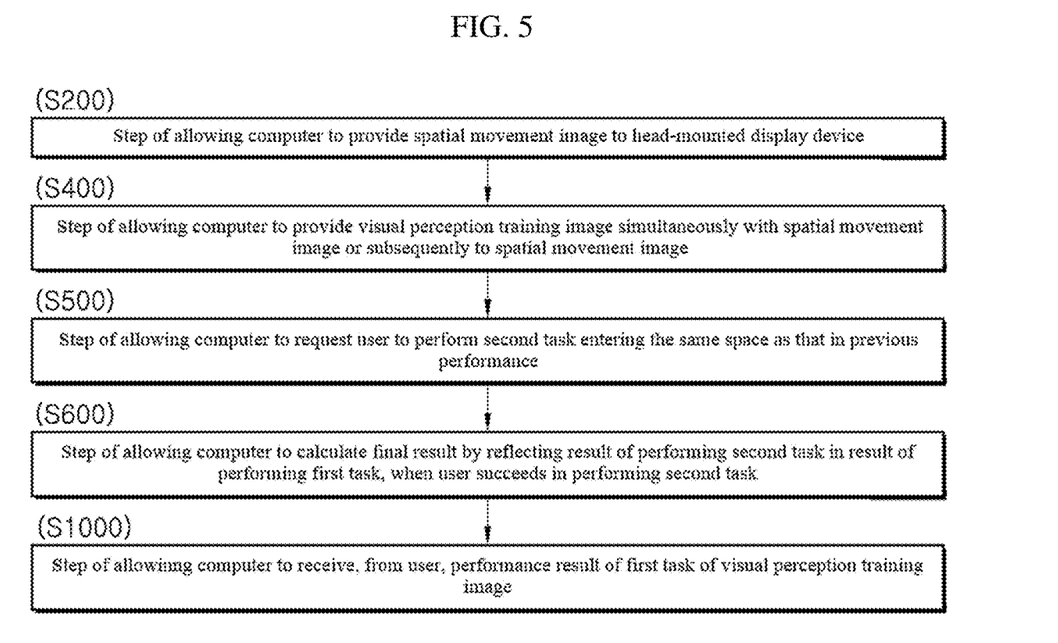
FIG. 5 is a flowchart illustrating a brain connectivity-based visual perception training method, which further includes a process of performing a second task entering the same space as that in previous performance, according to an embodiment of the inventive concept.
Figure 6:
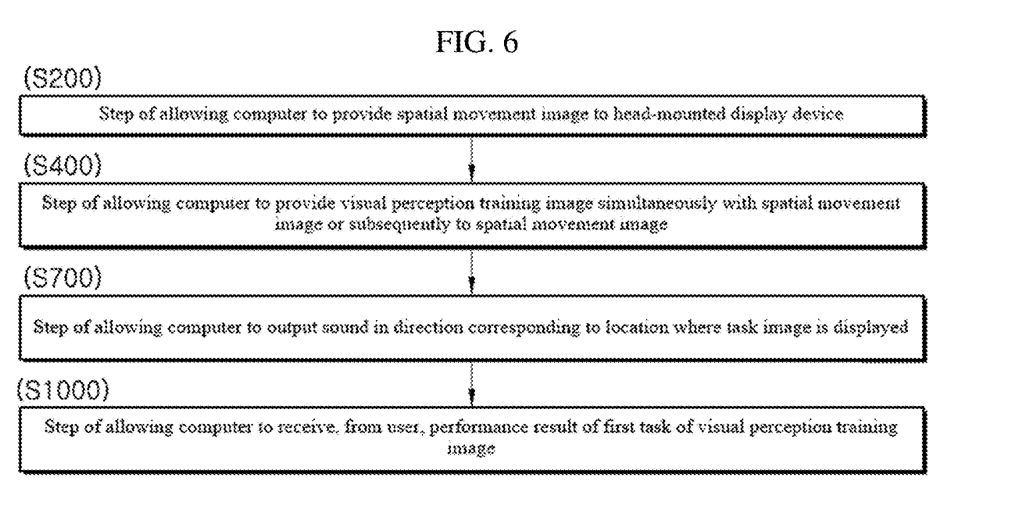
FIG. 6 is a flowchart illustrating a brain connectivity-based visual perception training method, which further includes a process of providing an acoustic output in the direction of outputting a task image, according to an embodiment of the inventive concept.
Figure 7:
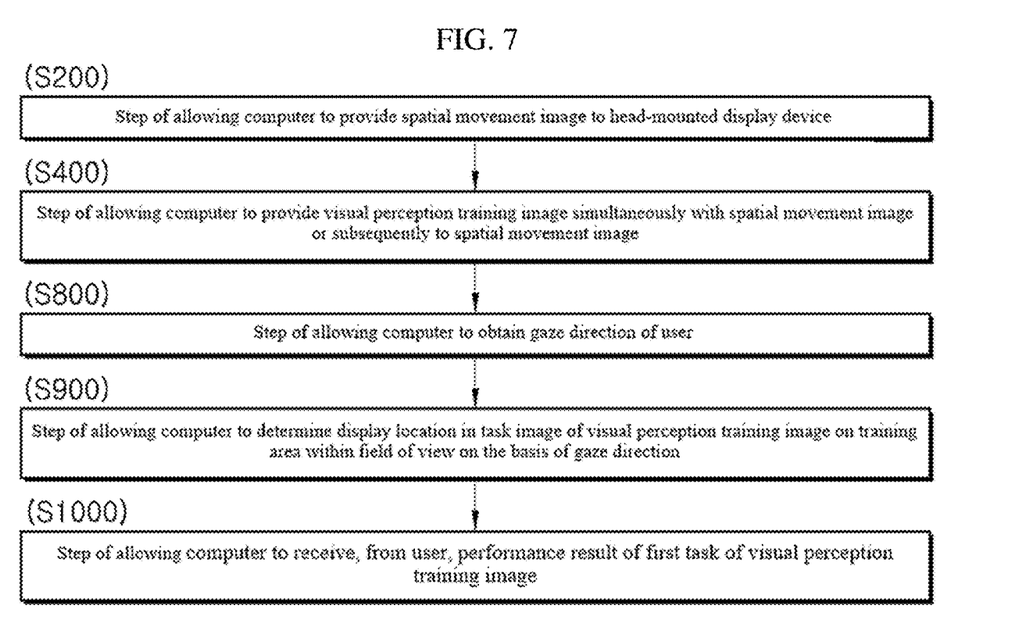
FIG. 7 is a flowchart illustrating a brain connectivity-based visual perception training method, which further includes a process of adjusting an output location of a task image in the direction of a field of view, according to an embodiment of the inventive concept.

FIG. 1 is a flowchart illustrating a brain connectivity-based visual perception method according to an embodiment of the inventive concept. FIG. 2 is a drawing illustrating a radial maze which is a virtual space for generating a spatial movement image according to an embodiment of the inventive concept. FIG. 3A is a drawing illustrating a field of view seen by a normal person, and FIGS. 3B and 3C are drawings illustrating a field of view seen by a patient with a visual perception disability according to brain damage. FIG. 4 is a drawing illustrating a visual perception training image provided in a specific space after performing spatial movement according to an embodiment of the inventive concept. FIG. 5 is a flowchart illustrating a brain connectivity-based visual perception training method, which further includes a process of performing a second task entering the same space as that in previous performance, according to an embodiment of the inventive concept. FIG. 6 is a flowchart illustrating a brain connectivity-based visual perception training method, which further includes a process of providing an acoustic output in the direction of outputting a task image, according to an embodiment of the inventive concept. FIG. 7 is a flowchart illustrating a brain connectivity-based visual perception training method, which further includes a process of adjusting an output location of a task image in the direction of a field of view, according to an embodiment of the inventive concept.

Referring to FIG. 1, the brain connectivity-based visual perception method according to an embodiment of the inventive concept may include providing (S200), by a computer, a spatial movement image to a head-mounted display device, providing (S400), by the computer, a visual perception training image 200 simultaneously with the spatial movement image or subsequently to the spatial movement image, and receiving (S1000), by the computer, the result of performing a first task 210 of the visual perception training image 200 from a user. Hereinafter, each step will be described in detail.

The visual cortex is an area located on the occipital lobe involved in directly processing visual information in the cerebral cortex. A sensation area of the cerebral cortex receives and processes signals input from somatesthesia, such as tactile sensation or nociception, and each of sensory organs, such as the sense of sight, the sense of hearing, the sense of taste, or the sense of smell, to be recognized and perceived. When a problem occurs in one of these paths, it may be impossible to perceive corresponding sensation. In detail, in a process where a person recognizes a sensory stimulus (e.g., a visual stimulus), after the sensory stimulus (e.g., the visual stimulus) is input to a sensory organ (e.g., eyes) to perform sensation, a sensation area (e.g., the visual cortex) of the cerebrum is perceived and recognition of uniting a sensory representation (e.g., a visual representation) into a memory representation to derive a meaning is performed. In this case, when the visual cortex is damaged when the sensory organ receives a visual stimulus, there is no abnormality in the sensory process of the sensory organ, but the visual stimulus is not perceived such that a person does not see an object.

The hippocampus is a part of the cerebral cortex which protrudes on a bottom surface of the inferior horn of lateral ventricle of the cerebrum, which is an area which is in close neural contact with the hypothalamus and is not seen outwardly. The hippocampus is an area playing an important role in long-term memory and space search. Among patients who have the damaged visual cortices and do not see objects, there is a patient who is able to recognize objects by redeeming the visual cortex where the hippocampus is damaged. In other words, the hippocampus is in close neural contact with the visual cortex of the cerebrum to have connectivity.

Thus, as the visual cortex and the hippocampus are stimulated together, the damaged or degraded visual perception capability may be improved. In detail, in the human brain, a brain area (e.g., a primary visual area, the parietal lobe, or the frontal lobe) for performing visual-spatial egocentric (sensory receptor centric) processing and the hippocampus for performing visual-spatial allocentric (visual-spatial environment itself) processing have brain connectivity. In other words, the hippocampus taking charging of visual-spatial memory has an influence on the visual perception function. Thus, as navigation training for simulating the hippocampus taking charging of visual-spatial memory and visual perception training for providing a visual stimulus are provided together, an effect according to the visual perception training may be improved.

In step S200, a computer may provide the spatial movement image on a screen of a head mounted display device. The spatial movement image may be an image where a user moves along a path in a virtual space. As an embodiment, the spatial movement image may be an image which is changed as the user moves on a virtual space irrespective of an operation of the user. In other words, the spatial movement image may provide only movement of a visual space without entailing motion of the user. As a result, the computer may provide a visual space change to stimulate the hippocampus of the brain of the user.

As another embodiment, the spatial movement image may be an image which is moved in a virtual space by motion of the user. For example, the spatial movement image may be generated based on data obtained by sensing real walking of the user using a walking sensing device. The walking sensing device may be a virtual reality (VR) treadmill which allows the user to walk. As a result, the computer may allow the user to walk actually and may stimulate the hippocampus through motion in the same virtual space as that in recognizing a spatial space environment while the user moves in a real space.

The spatial movement image may be implemented in various types of spaces. As an embodiment, as shown in FIG. 2, the spatial movement image may be implemented in a form where the user moves in a virtual space in the form of a radial maze. In other words, in the virtual space in the form of the radial maze, a central area where the user starts to move is present and a plurality of paths on which it is possible for the user to move are present by being extended from the central area. In the virtual space in the form of the radial maze, an identification indication (e.g., a specific picture frame disposed on a wall surface of the virtual space, a vase placed on a specific location in the virtual space, or the like) allowing the user to identify each path may be disposed. In other words, the computer may allow the user to distinguish a specific path of the radial maze based on the identification indication. Furthermore, as another embodiment, the spatial movement image may be an image where the user moves in the form of a general maze. In this case, a structure of the general maze may be changed after a specific training period is ended. For example, because the user should perform training of remembering a maze structure while performing training one time, the structure of the general maze may be maintained. When the user starts to perform new training after ending the training one time, the structure of the general maze may be changed.

The spatial movement image may be implemented in the form of providing a previously generated and stored frame over time or depending on an operation of the user. Furthermore, the spatial movement image may be implemented as a real-time image calculated based on a location of the user in a specific virtual space or a gaze direction of the user.

In step S400, the computer may provide the visual perception training image 200 simultaneously with the spatial movement image or subsequently to the spatial movement image. The visual perception training image 200 may be an image providing a task (i.e., a first task 210) for training to an area (i.e., a visual perception training area) which needs visual perception training within a field of view.

When the user is a patient with a visual perception disability by brain abnormality, as shown in FIG. 3, as abnormality occurs in the visual cortex, he or she may not see a portion of the field of view. The computer may provide a task to a visual perception training area, which is not seen in the field of view, using the visual perception training image 200 to allow the user to give a correct answer to the task and may treat the visual perception disability.

Furthermore, when the user is a normal person who has no visual perception disability, his or her visual perception function may belong to a normal range, but may be degraded, for example, a response to a visual stimulus is not quick. In this case, visual perception training may be performed to improve the visual perception function.

The first task 210 may provide questions the user should answer on a specific area in a screen (i.e., the visual perception training image 200). The first task 210 may be provided on the screen in various forms. As an embodiment, the computer may provide a question distinguishing different figures or patterns as the first task 210. For example, the computer may provide a question distinguishing a horizontal stripe pattern or a vertical stripe pattern as the first task 210 on the visual perception training area.

Furthermore, as another embodiment, when the visual perception training image 200 is provided together with the spatial movement image, the first task 210 may correspond to a task which should be performed in the spatial movement image. For example, when the spatial movement image of a virtual space is changed by real walking motion of the user, the computer may provide an instruction to perform a direction change (e.g., an arrow instructing to perform a path change in a specific direction or guidance for a location where a direction change should be performed) as the first task 210 on the visual perception training area in the visual perception training image 200. The computer may determine whether the user recognizes the first task 210 using whether the user performs motion corresponding to the first task 210. For example, when displaying an arrow guiding the user to perform a direction change and guidance information indicating the remaining distance until performing the direction change on the visual perception training area (e.g., an area which is not seen according to damage of the visual cortex or an area with a degraded visual perception capability) in a process where the user walks in the virtual space, the computer may determine that the user does not recognize the first task 210 when the user performs a path change in a different direction from the direction where the user is guided or when the user performs a path change at a different location from the point where the user is guided.

Furthermore, as another embodiment, when providing the visual perception training image 200 subsequently to the spatial movement image in step S400 and when the user enters any one of a plurality of spaces which are present in the virtual space by moving along the path, the computer may generate and provide the visual perception training image 200 based on a condition assigned to each space. The spatial movement image may include a plurality of divided spaces. As the user remembers a structure of the virtual space, he or she stimulates his or her hippocampus through a process where he or she moves along the path in the spatial movement image to enter a specific space. For example, when the user moves along the path on a radial maze, the computer may provide the user with the visual perception training image 200 in a space (i.e., a divided space) at the end of each path.

In this case, a condition of providing the visual perception training image 200 may be assigned to each divided space. The condition of providing the visual perception training image 200 may correspond to whether the visual perception training image 200 is provided in a divided space in the virtual space where the user moves, a level of a reward provided when the visual perception training image 200 is provided, or the like. For example, the computer may provide only some of the plurality of divided spaces with the visual perception training image 200. When the reward is provided as the user performs visual perception training, the computer may set the reward such that the user does not obtain the reward when the user enters a divided space which does not provide the visual perception training image 200. Furthermore, for example, the computer may differently set the reward obtained as the user performs visual perception training when each divided space provides the visual perception training image 200.

For example, when the user performs spatial movement on a radial maze in the virtual space, the computer may perform visual perception training for only providing a reward at the end of a path matched to a specific condition (i.e., a condition set for each condition) among a plurality of radial paths and, as a result, may allow the user to search for and remember the path matched to the condition.

Furthermore, for example, when the user repeatedly performs a path search, as he or she searches for a path corresponding to a reward providing condition for the first time and memorizes the same or different path corresponding to the reward providing condition in next performance (e.g., performance of starting to perform a path search again in the center of a radial maze or searching for another divided space at a location where the first task 210 is provided) to move, the hippocampus may be stimulated. In other words, when allowing the user to repeatedly perform the second task of searching for a path, the computer may provide the user with a higher reward when the user finds the path which provides the reward in the same manner or may not provide the user with the reward when the user finds the path where the user has already moved to guide the user to remember the space.

By providing the visual perception training image 200 according to the providing condition in the space the user enters, the computer may provide the user with a training process of stimulating the visual cortex subsequently to the training process of stimulating the hippocampus.

Furthermore, as another embodiment, when providing the visual perception training image 200 simultaneously with the spatial movement image in step S400, the computer may combine and provide frames of the visual perception training image 200, which are generated at intervals of a unit time, on the spatial movement image. For example, the computer may combine a first image frame included in the spatial movement image with a second image frame included in the visual perception training image 200 to generate a final output image.

In this case, as an embodiment, the first image frame may be changed by head motion or pupil motion of the user, and the second image frame may be fixed without being changed by the head motion or the pupil motion of the user. Although the user moves his or her head or gaze in the process of moving in the virtual space, he or she may train a damaged visual cortex area only when the first task 210 should be displayed on a visual perception training area. When the first task 210 is changed in location as the user moves his or her head or pupils, as the first task 210 is displayed on a normal area in a field of view, the user may identify the first task 210. Thus, to fix the first task 210 to the visual perception training area, the computer may set the second image frame included in the visual perception training image 200 to be fixed irrespective of head motion or pupil motion.

In step S1000, the computer may receive the result of performing the first task 210 of the visual perception training image 200 from the user. When providing the visual perception training image 200 after providing the spatial movement image on a screen of the head-mounted display device, the computer may determine whether a correct answer is input to the first task 210 of the visual perception training image 200 provided in the space the user enters. In other words, as shown in FIG. 4, the first task 210 may be a question provided at a specific location on a two- or three-dimensional (2D or 3D) space (e.g., a question for selecting a figure displayed on a visual perception training area among several figures), and the result of performing the first task 210 may be whether an input value to the question displayed on the visual perception training area is a correct answer.

When the spatial movement image and the visual perception training image 200 are provided together, the first task 210 may be displayed on the visual perception training area in the visual perception training image 200 and should be performed when the user walks, and the result of performing the first task 210 may be whether the user who is walking performs motion corresponding to the first task 210. In other words, when providing the spatial movement image and the visual perception training image 200 simultaneously, the computer may allow the user to enter an answer to a question in the visual perception training image 200.

As an embodiment, the computer may receive a correct answer to the first task 210 displayed at one side while the user moves in the virtual space corresponding to the spatial movement image, via controllers held in both his or her hands. For a question for selecting a figure included in the first task 210 between two first and second figures, the computer may match the first figure to a left controller and may match the second figure to a right controller, thus receiving a correct answer depending on a type of a controller operated by the user.

Furthermore, as another embodiment, when the first task 210 is an operation or motion which should be performed while the user moves in a virtual space corresponding to the spatial movement image, the computer may determine whether the user visually recognizes the first task 210 based on whether the user performs the operation or motion according to the first task 210 after the first task 210 is provided on the screen. For example, when the operation or motion is a change in the walking direction of the user, the computer may identify whether the user visually recognizes the first task 210 based on whether the user changes the walking direction. Furthermore, furthermore, the computer may determine a motion type of the user using a vision sensor or a motion sensor for recognizing motion of the user and may determine whether the motion of the user is an operation corresponding to the first task 210.

The computer may calculate the result of performing the visual perception training based on the result of performing the first task 210 and may determine a visual perception function state of the user.

Furthermore, as another embodiment, as shown in FIG. 5, the brain connectivity-based visual perception method may further include requesting (S500), by the computer, the user to perform a second task entering the same space as that in previous performance, when providing the visual perception training image 200 subsequently to the spatial movement image, and calculating (S600), by the computer, a final result by reflecting the result of performing the second task in the result of performing the first task 210, when the user succeeds in performing the second task. By allowing the user to perform spatial movement, remember a path where the user moves in the space, and re-perform the spatial movement, the compute may stimulate the hippocampus which takes charge of remembering the space and is associated with a visual perception function. In other words, the second task may be a task of allowing the user to remember the same path as that in previous performance in the virtual space in the spatial movement image and move along the path.

In step S500, the computer may request the user to perform the second task entering the same space as that in previous performance again. For example, the computer may change a location where the user starts to perform spatial movement in the same virtual space having a plurality of divided spaces and may request the user to search for the same space. In other words, the computer may allow the user to remember a space structure identified while the user moves in the virtual space in the previous performance process to stimulate the hippocampus, may stimulate the hippocampus through brain connectivity to improve the visual perception function.

Thereafter, when the user succeeds in performing the second task, in step S600, the computer may calculate a final result by reflecting the result of performing the second task in the result of performing the first task 210. In other words, when the hippocampus is stimulated by remembering the space when the user succeeds in performing the second task searching for the same space, the computer may calculate a final result of visual perception training by reflecting whether the user succeeds in performing the second task together with the result of performing the first task 210 of performing the visual perception training in the specific space.

Furthermore, as another embodiment, as shown in FIG. 6, the brain connectivity-based visual perception method may further include outputting, by the computer, a sound in a direction corresponding to a location where the first task 210 (or a task image) is displayed. Because a patient who does not see a portion of his or her field of view due to his or her brain damage may visually recognize the task image 210 in the visual perception training image 200, the computer may guide the patient in the direction of providing a visual perception stimulus through another sensation. The computer may provide a sound in a direction corresponding to a location where the task image 210 is displayed by outputting a 3D sound, thus improving the visual perception function through an attempt to recognize the task image 210 in a field of view in the direction where the sound is provided.

Furthermore, as another embodiment, as shown in FIG. 7, the brain connectivity-based visual perception method may further include obtaining (S800), by the computer, a gaze direction of the user and determining (S900), by the computer, a display location in the task image 210 of the visual perception training image 200 on a training area in a field of view on the basis of the gaze direction. There is a need to prevent the first task 210 (i.e., the task image) from being located on a normal area without being disposed on a visual perception training area (e.g., a visual damage area) by gaze movement of the user. To this end, the computer may measure a gaze direction of the user in real time and may adjust a location of the first task 210 to the visual perception training area on the basis of the gaze direction (i.e., the center of the field of view in the direction the user is looking). The gaze direction may be determined by head motion and pupil motion. The computer may identify head motion of the user by means of a motion sensor provided in the head-mounted display device. Furthermore, the computer may identify pupil motion of the user by means of an eye-tracker provided in the head-mounted display device.

In detail, in step S800, the computer may obtain a gaze direction (i.e., a direction of the center of a field of view the user is looking) by means of the motion sensor or the eye-tracker in the head-mounted display device. Thereafter, in step S900, the computer may determine a visual perception training area on the basis of the gaze direction and may adjust a display location in the virtual space of the first task 210 (i.e., the task image 210). For example, when a left upper area relative to the center of a field of view is an area which is not seen due to brain abnormality and when the gaze direction is changed by head motion or pupil motion of the user, the computer may identify the changed gaze direction, may determine a field of view of the user on the basis of the gaze direction, and may adjust a range corresponding to the left upper end of the field of view to a visual perception training area on the basis of the gaze direction to display the first task 210.

The head-mounted display device according to another embodiment of the inventive concept may provide a spatial movement image on a screen of the head-mounted display device, may provide a visual perception training image, including a first task, simultaneously with the spatial movement image or subsequently to the spatial movement image, and may calculate a final result of visual perception training based on the result of performing the first task of the visual perception training image or may transmit the result of performing the first task to a computing device which calculates the final result. The result of performing the first task may be generated by determining whether a user operation received from the user is identical to the first task. The user operation may be input via a controller connected with the head-mounted display device. The controller may include a device held and used by the user, a walking sensing device on which the user sits and walks, or the like. The spatial movement image may be an image where the user moves along a path in a virtual space.

Figure 8:
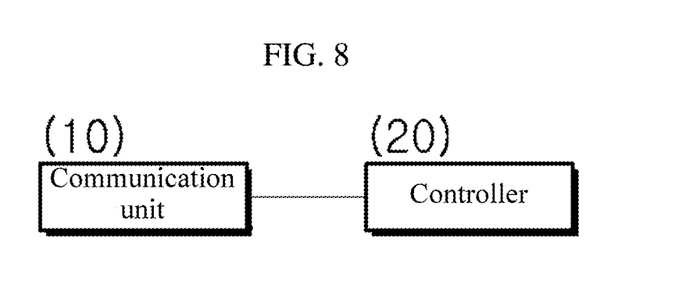
FIG. 8 is a block diagram illustrating an internal configuration of a brain connectivity-based visual perception training computing device according to another embodiment of the inventive concept.

FIG. 8 is a block diagram illustrating an internal configuration of a brain connectivity-based visual perception training computing device according to another embodiment of the inventive concept.

Referring to FIG. 8, the brain connectivity-based visual perception training computing device according to another embodiment of the inventive concept may provide a spatial movement image to a head-mounted display device or a client device connected with the head-mounted display device, may provide a visual perception training image 200 simultaneously with the spatial movement image or subsequently to the spatial movement image, and may receive the result of performing a first task 210 of the visual perception training image 200 from a user. The spatial movement image may be an image where the user moves along a path in a virtual space.

The brain connectivity-based visual perception training computing device according to another embodiment of the inventive concept may include a communication unit 10 and a controller 20.

The controller 20 may play a role in generating a spatial movement image for a specific virtual space or extracting a previously stored spatial movement image in real time. The spatial movement image may be an image where the user moves along a path in a virtual space. As an embodiment, the spatial movement image may be an image which is changed as the user moves in a virtual space irrespective of an operation of the user. In other words, the spatial movement image may provide only movement of a visual space without entailing motion of the user. As a result, the controller 20 may provide a visual space change to stimulate the hippocampus of the brain of the user. As another embodiment, the spatial movement image may be an image which is moved in a virtual space by motion of the user. For example, the spatial movement image may be generated based on data obtained by sensing real walking of the user using a walking sensing device. The walking sensing device may be a virtual reality (VR) treadmill which allows the user to walk. As a result, the controller 20 may allow the user to walk actually and may stimulate the hippocampus through motion in the same virtual space as that in recognizing a spatial space environment while the user moves in a real space.

Furthermore, as another embodiment, the controller 20 may provide the spatial movement image based on various types of spaces. For example, the controller 20 may generate an image where the user moves as the spatial movement image in the form of a radial maze or a general maze.

Furthermore, as another embodiment, when applying a structure of the general maze to a virtual space, the controller 20 may change a maze structure after a specific training period is ended. For example, because the user should perform training of remembering a maze structure while performing training one time, the structure of the general maze may be maintained. When the user starts to perform new training after ending the training one time, the structure of the general maze may be changed.

Furthermore, as another embodiment, the controller 20 may implement frames of the spatial movement image, which are previously generated and stored, in the form of being provided over time or depending on an operation of the user. Furthermore, as another embodiment, the controller 20 may implement the spatial movement image as a real-time image calculated based on a location of the user in a specific virtual space or a gaze direction of the user.

Furthermore, the controller 20 may play a role in providing the visual perception training image 200 simultaneously with the spatial movement image or subsequently to the spatial movement image. The visual perception training image 200 may be an image providing a task (i.e., a first task 210) for training on an area (i.e., a visual perception training area) which needs visual perception training within a field of view. The first task 210 may provide a question the user should answer on a specific area in a screen (i.e., the visual perception training image 200).

The first task 210 may be provided on the screen in various forms. As an embodiment, the controller 20 may provide a question distinguishing different figures or patterns as the first task 210. For example, the controller 20 may provide a question distinguishing a horizontal stripe pattern or a vertical stripe pattern as the first task 210 on the visual perception training area.

Furthermore, as another embodiment, when the visual perception training image 200 is provided together with the spatial movement image, the first task 210 may correspond to a task which should be performed in the spatial movement image. For example, when the spatial movement image of a virtual space is changed by real walking motion of the user, the controller 20 may provide an instruction to perform a direction change (e.g., an arrow instructing to perform a path change in a specific direction or guidance for a location where a direction change should be performed) as the first task 210 on the visual perception training area in the visual perception training image 200.

Furthermore, as another embodiment, when providing the visual perception training image 200 subsequently to the spatial movement image and when the user enters any one of a plurality of spaces which are present in the virtual space by moving along a path in the virtual space, the controller 20 may generate and provide the visual perception training image 200 based on a condition assigned to each space. The spatial movement image may include a plurality of divided spaces. As the user remembers a structure of a virtual space, he or she stimulates his or her hippocampus through a process where he or she moves along a path in the spatial movement image and enters a specific space. For example, when the user moves along a path on a radial maze, the controller 20 may provide the user with the visual perception training image 200 in a space (i.e., a divided space) at the end of each path. In this case, a condition of providing the visual perception training image 200 may be assigned to each divided space. A detail description of the condition of providing the visual perception training image, which is described above, will be omitted. By providing the visual perception training image 200 according to the condition in the space the user enters, the controller 20 may provide the user with a training process of stimulating the visual cortex subsequently to the training process of stimulating the hippocampus.

Furthermore, as another embodiment, when providing the spatial movement image as the user moves along a path in a virtual space and when providing the visual perception training image 200 subsequently to the spatial movement image as the user enters any one of a plurality of divided spaces present in the virtual space, the controller 20 may generate the visual perception training image 200 depending on the visual perception training image providing condition assigned to each divided space the user enters. The visual perception training image providing condition may be whether the visual perception training image 200 is provided in each divided space or a level of a reward provided when the visual perception training image 200 is provided in each divided space.

Furthermore, as another embodiment, the controller 20 may request the user to perform a second task entering the same space as that in previous performance and may calculate a final result by reflecting the result of performing the second task in the result of performing the first task 210 when the user succeeds in performing the second task.

Furthermore, as another embodiment, when providing the visual perception training image 200 simultaneously with the spatial movement image, the controller 20 may play a role in combining and providing frames of the visual perception training image 200, which are generated at intervals of a unit time, on the spatial movement image. For example, the controller 20 may combine a first image frame included in the spatial movement image with a second image frame included in the visual perception training image 200 to generate a final output image. In this case, as an embodiment, the first image frame may be changed by head motion or pupil motion of the user, and the second image frame may be fixed without being changed by the head motion or the pupil motion of the user. Although the user moves his or her head or gaze in the process of moving in the virtual space, he or she may train a damaged visual cortex area only when the first task 210 should be displayed on a visual perception training area.

Furthermore, the controller 20 may receive the result of performing the first task 210 of the visual perception training image 200 from the user. The controller 20 may receive the result of performing the first task 210 from a controller connected with a head-mounted display device or a client device connected with the head-mounted display device. The controller may be a device operated in a state held by the user and may be a device where the user performs motion such as walk in a state where the user sits. For example, the controller 20 may generate the spatial movement image based on data obtained by sensing real walking of the user using a walking sensing device.

In detail, the controller 20 may receive a correct answer to the first task 210 displayed at one side while the user moves in the virtual space corresponding to the spatial movement image, as the result of performing the first task 210 input via controllers held in both his or her hands. Furthermore, the controller 20 may receive an operation or motion, which should be performed while the user moves in the virtual space corresponding to the spatial movement image, as the result of performing the first task 210. In other words, the controller 20 may simultaneously provide the spatial movement image as the user moves along a path and the visual perception training image 200 displaying the first task 210 on the visual perception training area, may receive motion of the user, corresponding to the first task 210 while the user moves along the path, and may calculate the result of performing the first task 210. For example, when providing the visual perception training image 200 as an image for instructing the user to change a walking direction, the controller 20 may receive an operation or motion where the user performs a direction change at a specific time in a specific direction as the result of performing the first task 210.

Furthermore, the controller 20 may play a role in calculating the result of performing visual perception training based on the result of performing the first task 210. Furthermore, the controller 20 may play a role in identifying a visual perception function state of the user based on the result of performing the visual perception training.

As an embodiment, when the first task 210 is an operation or motion which should be performed while the user moves in the virtual space corresponding to the spatial movement image, the controller 20 may determine whether the user visually recognizes the first task 210 based on whether the user performs the operation or motion according to the first task 210 after the first task 210 is provided on the screen. Furthermore, as another embodiment, when providing the visual perception training image 200 after providing the spatial movement image on a screen of the head-mounted display device, the controller 20 may determine whether a correct answer is input to the first task 210 of the visual perception training image 200 provided in the space the user enters.

The communication unit 10 may provide the spatial movement image to the head-mounted display device or a client device connected with the head-mounted display device. The computing device may be a server device. When the head-mounted display device is connected to the client device to display a provided image, the communication unit 10 may transmit the spatial movement image to the client device. When the computing device is a client device connected with the head-mounted display device, it may generate the spatial movement image and may provide the spatial movement image to the head-mounted display device. A brain connectivity-based visual perception training device according to another embodiment of the inventive concept may provide a spatial movement image providing path movement of the user in a virtual space, may provide a visual perception training image simultaneously with the spatial movement image or subsequently to the spatial movement image, and may receive the result of performing a first task of the visual perception training image.

As an embodiment, the visual perception training device may include the controller 20. The controller 20 may play a role in providing a spatial movement image providing path movement of the user in a virtual space and providing a visual perception training image simultaneously with the spatial movement image or subsequently to the spatial movement image.

The above-mentioned brain connectivity-based visual perception training method according to an embodiment of the inventive concept may be combined with a computer which is hardware and may be stored in a medium to be implemented as a program (or application) to be executed.

For the computer to read the program and execute the methods implemented with the program, the above-mentioned program may include a code coded into a computer language such as C, C++, Java, or a machine language readable through a device interface of the computer by a processor (CPU) of the computer. Such a code may include a functional code associated with a function and the like defining functions necessary for executing the methods and may include a control code associated with an execution procedure necessary for the processor of the computer to execute the functions according to a procedure. Further, such a code may further include a code associated with memory reference about whether additional information or media necessary for the processor of the computer to execute the functions is referred at any location (address number) of an internal or external memory of the computer. Further, if it is necessary for the processor of the computer to communicate with any computer or server located in a remote place to execute the functions, the code may further include a communication related code about how communication is performed with any computer or server located in a remote place using a communication module of the computer and whether to transmit and receive any information or media upon communication.

The medium may refer to a device-readable medium which stores data on a semipermanent basis rather than a medium, such as a register, a cache, or a memory, which stores data during a short moment. The medium may refer to a device-readable medium which stores data on a semipermanent basis rather than a medium, such as a register, a cache, or a memory, which stores data during a short moment. In other words, the program may be stored in various storage media on various servers accessible by the computer or various storage media on the computer of the user. Further, the medium may be distributed to a computer system connected over a network and may store a computer-readable code on a distributed basis.

According to an embodiment of the inventive concept, the brain connectivity-based visual perception training device may train the visual cortex and the hippocampus, which have brain connectivity, together, thus improving a visual perception function which is higher than that when performing visual perception training for the visual cortex.

Furthermore, the brain connectivity-based visual perception training device may provide spatial movement and visual perception training sequentially or simultaneously, thus providing various training forms of training the visual cortex and the hippocampus together.

Furthermore, the brain connectivity-based visual perception training device may provide a second task of searching for the same space to allow the user to remember a space form where spatial movement is performed, thus enhancing a hippocampus stimulation effect.

Furthermore, the brain connectivity-based visual perception training device may provide a first task corresponding to a visual perception stimulus as an instruction to perform a specific operation in the process of performing the spatial movement, thus providing training in the form of interesting content. In other words, the brain connectivity-based visual perception training device may more provide the user with interest upon training while more enhancing the effect of improving the visual perception function (i.e., a treatment effect) than an existing technology.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A brain connectivity-based visual perception training method, the method comprising:
providing, by a computer, a spatial movement image to a head-mounted display device, wherein the spatial movement image is a video image showing a visual space change to implement a movement of a user along a path in a virtual space;
providing, by the computer, a visual perception training image simultaneously with the spatial movement image or subsequently to the spatial movement image, wherein the visual perception training image is an image showing a first task to be performed in a visual perception training area, which corresponds to an area within a field of view of the user, that needs visual perception training; and
receiving, by the computer, a result of performing the first task of the visual perception training image from the user.

2. The method of claim 1, wherein the providing of the visual perception training image includes:
when providing the visual perception training image subsequently to the spatial movement image, generating and providing, by the computer, the visual perception training image based on a condition assigned to each space, when the user enters any one of a plurality of spaces present in the virtual space by moving along the path.

3. The method of claim 2, further comprising:
requesting, by the computer, the user to perform a second task that repeats the movement of the user in the virtual space, shown in the video image of the spatial movement image; and
calculating, by the computer, a final result by reflecting a result of performing the second task in the result of performing the first task, when the user succeeds in performing the second task.

4. The method of claim 1, wherein the providing of the visual perception training image includes:
when providing the visual perception training image simultaneously with the spatial movement image, combining and providing frames of the visual perception training image, the frames being generated at intervals of a unit time, on the spatial movement image.

5. The method of claim 4, wherein the first task is a task which should be performed by the user upon walking and is displayed on the visual perception training area of the user in the visual perception training image, and
wherein the result of performing the first task is whether the user who is walking performs motion corresponding to the first task.

6. The method of claim 4, wherein the providing of the visual perception training image includes:
generating a final output image by combining a first image frame included in the spatial movement image with a second image frame included in the visual perception training image,
wherein the first image frame is changed by head motion or pupil motion of the user, and
wherein the second image frame is fixed without being changed by the head motion or the pupil motion of the user.

7. The method of claim 1, wherein the spatial movement image is generated based on data obtained by sensing real walking of the user using a walking sensing device.

8. The method of claim 1, wherein the visual perception training image displays a task image on the visual perception training area of the user in the visual perception training image,
further comprising:
outputting, by the computer a sound in a direction corresponding to a location where the task image is displayed.

9. The method of claim 1, further comprising:
obtaining, by the computer, a gaze direction of the user; and
determining, by the computer, a display location in a task image of the visual perception training image on the visual perception training area in the field of view of the user on the basis of the gaze direction.

10. The method of claim 1, wherein the visual perception training area is determined based on information of an area which is not seen by the user according to damage of a visual cortex of the user or based on information on an area with a degraded visual perception capability of the user.

11. The method of claim 10, wherein the spatial movement image is configured to stimulate a hippocampus that has a connectivity with the visual cortex of the user.

12. The method of claim 1, wherein the spatial movement image is the video image showing the visual space change to implement the movement of the user in the virtual space that is a maze, and
wherein a structure of the maze is configured to be changed after a specific training period is ended.

13. A non-transitory computer readable recording medium storing a brain connectivity-based visual perception training program, coupled to a hardware computer device, the program being configured to execute the method of claim 1.

14. A brain connectivity-based visual perception training computing device, the computing device comprising:
a processor configured to:
provide a spatial movement image to a client device connected with a head-mounted display device or the head-mounted display device, wherein the spatial movement image is a video image showing a visual space change to implement a movement of a user along a path in a virtual space;
provide a visual perception training image simultaneously with the spatial movement image or subsequently to the spatial movement image, wherein the visual perception training image is an image showing a first task to be performed in a visual perception training area, which corresponds to an area within a field of view of the user, that needs visual perception training;
receive a result of performing the first task of the visual perception training image from the user; and
calculate a final result of visual perception training.

15. The computing device of claim 14, wherein, when providing the spatial movement image as the user moves along the path in the virtual space and when providing the visual perception training image subsequently to the spatial movement image as the user enters any one of a plurality of divided spaces present in the virtual space, the processor is further configured to generate the virtual perception training image depending on a virtual perception training image providing condition assigned to each divided space the user enters, and wherein the virtual perception training image providing condition is whether the visual perception training image is provided in each divided space or a level of a reward provided when the visual perception training image is performed in each divided space.

16. The computing device of claim 15, wherein the processor is further configured to request the user to perform a second task that repeats the movement of the user in the virtual space, shown in the video image of the spatial movement image, and calculate the final result by reflecting a result of performing the second task in the result of performing the first task, when the user succeeds in performing the second task.

17. The computing device of claim 14, wherein the processor is further configured to simultaneously provide the spatial movement image as the user moves along the path and the visual perception training image displaying the first task on the visual perception training area and receive motion of the user, the motion corresponding to the first task, while the user moves along the path, and calculate the result of performing the first task.

18. The computing device of claim 14, wherein the processor is further configured to generate the spatial movement image based on data obtained by sensing real walking of the user using a walking sensing device.

19. A head-mounted display device, comprising:
a processor for:
providing a spatial movement image on a screen of the head-mounted display device wherein the spatial movement image is a video image showing a visual space change to implement a movement of a user along a path in a virtual space;
providing a visual perception training image, including a first task, simultaneously with the spatial movement image or subsequently to the spatial movement image, wherein the visual perception training image is an image showing a first task to be performed in a visual perception training area, which corresponds to an area within a field of view of the user, that needs visual perception training; and
calculating a final result of visual perception training based on a result of performing the first task of the visual perception training image or transmitting the result of performing the first task to a computing device configured to calculate the final result,
wherein the result of performing the first task is generated by determining whether a user operation received from a user is identical to the first task, and
wherein the user operation is input via a controller connected with the head-mounted display device.

20. A brain connectivity-based visual perception training device, comprising:
a processor for:
providing a spatial movement image providing path movement of a user in a virtual space wherein the spatial movement image is a video image showing a visual space change to implement a movement of a user along a path in a virtual space;
providing a visual perception training image simultaneously with the spatial movement image or subsequently to the spatial movement image, wherein the visual perception training image is an image showing a first task to be performed in a visual perception training area, which corresponds to an area within a field of view of the user, that needs visual perception training; and
receiving a result of performing the first task of the visual perception training image from the user.

* * * * *